United States Patent [19]
Korf

[11] Patent Number: 5,039,515
[45] Date of Patent: Aug. 13, 1991

[54] MOUTH CLEANSING PREPARATION

[76] Inventor: Patricia K. Korf, 6255 Stagecoach Dr., Sacramento, Calif. 95842

[21] Appl. No.: 617,015

[22] Filed: Nov. 21, 1990

[51] Int. Cl.$^5$ .................. A61K 7/20; A61K 33/08; A61K 33/10; A61K 33/40
[52] U.S. Cl. .................................... 424/53; 424/613; 424/616; 424/686; 424/687; 424/690; 424/691; 424/692
[58] Field of Search ............ 424/49, 52, 53, 613–616, 424/686, 687, 690, 691, 692

[56] References Cited

U.S. PATENT DOCUMENTS

| | | | |
|---|---|---|---|
| 1,018,240 | 2/1912 | Von Foregger | 424/53 |
| 2,054,742 | 9/1936 | Elbel | 424/53 |
| 2,218,172 | 10/1940 | Kokatnur | 424/53 |
| 3,887,712 | 6/1975 | Lover et al. | 424/52 |
| 4,209,505 | 6/1980 | Mikhail | 424/54 |
| 4,431,631 | 2/1984 | Clipper et al. | 424/53 |
| 4,476,108 | 10/1984 | Kessler et al. | 424/53 |
| 4,528,180 | 7/1985 | Schaeffer | 424/53 |
| 4,567,036 | 1/1986 | Simon et al. | 424/53 |
| 4,684,571 | 8/1987 | Clipper et al. | 424/53 |
| 4,687,663 | 8/1987 | Schaeffer | 424/53 |
| 4,776,500 | 10/1988 | Ford | 424/53 |
| 4,812,308 | 3/1989 | Winston et al. | 424/53 |
| 4,837,008 | 6/1989 | Rudy et al. | 424/53 |
| 4,839,157 | 6/1989 | Ng et al. | 424/53 |
| 4,849,213 | 7/1989 | Schaeffer | 424/53 |
| 4,867,988 | 9/1989 | Chernack | 424/53 |
| 4,891,211 | 1/1990 | Winston | 424/53 |
| 4,895,721 | 1/1990 | Drucker | 424/53 |
| 4,897,258 | 1/1990 | Rudy et al. | 424/53 |
| 4,971,782 | 11/1990 | Rudy et al. | 424/53 |
| 4,976,955 | 12/1990 | Libin | 424/53 |
| 4,980,154 | 12/1990 | Gordon | 424/53 |
| 4,983,379 | 1/1991 | Schaeffer | 424/53 |
| 5,000,941 | 3/1991 | Chernack | 424/53 |
| 5,000,942 | 3/1991 | Libin | 424/53 |

Primary Examiner—Shep K. Rose
Attorney, Agent, or Firm—James M. Ritchey

[57] ABSTRACT

A mouth cleansing composition for removing dried secretion deposits in and around a user's oral cavity is disclosed. The composition is a mixture of an aqueous salt containing solution, glycerin, hydrogen peroxide, and an acid neutralizing agent.

7 Claims, No Drawings

MOUTH CLEANSING PREPARATION

BACKGROUND OF THE INVENTION

1. Field of the Invention

A composition of matter and method of use are related in this disclosure for cleaning and removing secretions deposits from around and in the oral cavity a user or patient on which the subject composition is applied. Individuals suffering from numerous diseases or medical procedures that result is a dry mouth benefit from the subject composition.

2. Description of the Background Art

To facilitate the removal of secretion or other bodily fluid deposits in and around an individual's or particularly a medical patient's mouth, various solutions have been employed. Simply applying water to an area of dried secretions generally has a limited effect and generally fails to dissolve many combined or sole inorganic and organic materials that build up upon evaporation of normal or abnormal fluids about the mouth.

Specifically, U.S. Pat. No. 2,218,172 discloses a preparation for antisepsis of the oral cavity. Included in a substantially alkaline medium is an organic peroxidic compound and a solvent for both the peroxidic compound and saliva. During application of the preparation, oxygen is released, thereby destroying pathogenic organisms.

U.S. Pat. No. 3,887,712 presents oral hygiene products. Specifically, alexidine dihydrofluoride is used to treat dental plaque, calculus, gingivitis, caries, and related periodontal disease.

A pilocarpine mouthwash for dry mouth relief is described in U.S. Pat. No. 4,209,505. A sweetened mouthwash carrier contains pilocarpine nitrate or hydrochloride is contacted with the user's mucosal lining of the mouth.

An aqueous oral solution containing hydrogen peroxide, glycerin, and/or sorbital, pluronic-type surfactant, polyoxyethylenated sorbitol monofatty acid ester surfactant, sweetener, and selected flavor is disclosed in U.S. Pat. No. 4,431,631. This solution has 1–3% hydrogen peroxide and 3–15% glycerin or sorbitol.

U.S. Pat. No. 4,476,108 describes a bactericidal method. A bactericidal agent comprising a peroxidase enzyme system is employed during the treatment of dental disease or cleaning dentures to produce free radicals for killing bacteria.

A chemotherapeutic agent and method for treating periodontal disease is revealed in U.S. Pat. No. 4,567,036. The agent comprises an aqueous solution of hydrogen peroxide and a povidone-iodine complex. Treatment comprises swishing or rising the mouth with the solution.

U.S. Pat. No. 4,684,517 divulges a mouthrinse composition containing hydrogen peroxide and fluoride. This composition is an aqueous storage-stable mouthwash having a flavor mixture, 0.5–5% hydrogen peroxide, 0.01–2% fluoride.

Disclosed in U.S. Pat. No. 4,839,157 is a stable hydrogen peroxide dental gel dentifrice for oral anti-gingivitis application containing fumed silicas. Specifically, the composition comprises 1.5–3.5% hydrogen peroxide, hydrophilic and hydrophobic fumed silica gelling agents, 20–40% polyethylene glycol, humectant, a nonionic surfactant, sweetening agent, sodium benzoate, and flavor.

Related in U.S. Pat. No. 4,895,721 is a peroxide gel dentifrice composition. Viscosity variations are stabilized, as is peroxide loss. The composition comprises aqueous peroxide, polyols, gelling agent, and stabilizers. The gel liberates oxygen that kills harmful organisms.

SUMMARY OF THE INVENTION

An object of the present invention is to provide a cleansing or solvating agent for the removal of dried organic and inorganic materials from in and around a user's oral cavity.

An additional object of the present invention is to relate a method of removing secretion deposits from in and around a user's oral cavity.

A further object of the present invention is to describe a cleansing or solvating agent that is mild, yet effective at dislodging dried secretion deposits in the mouth and on the tongue of a user.

Provided by the subject composition is a mouth cleansing composition comprising an aqueous salt solution containing glycerin, aqueous hydrogen peroxide solution having about 3% hydrogen peroxide, and an acid neutralizing agent such as a liquid antacid. The glycerine, aqueous hydrogen peroxide solution having about 3% hydrogen peroxide, and acid neutralizing agent are present in about 5% to about 15%, by volume, amounts. The cleansing composition is applied to a swab for removal of the dried secretion deposits by actively scrubbing the dried secretion deposited areas.

Other objects, advantages, and novel features of the present invention will become apparent from the detailed description that follows, when considered in conjunction with the associated drawings.

DESCRIPTION OF THE PREFERRED EMBODIMENT

Following is described a preferred embodiment of a composition of matter and method of use for dissolving secretion deposits or mucus discharges that build up in and around an individual's oral cavity. Patients suffering from various metabolic imbalances and diseases, in particular those involving numerous malignancies, do not have sufficient quantities of liquid solvent (or the solvating properties of the liquid solvent are impaired) in their saliva to maintain normal solvation of dissolved solutes and suspended particles or other liquids. As a result, irritating and unsightly levels of these solutes, other liquids, and particles (secretion deposits) build up on a patient's tongue, on the walls of the oral cavity, and on the surrounding external areas of the mouth. To maintain a healthy oral environment and appearance, the secretion deposits are removed by application of the subject mouth cleansing composition.

The mouth cleansing preparation of the present invention comprises an aqueous salt solution containing glycerin, hydrogen peroxide, and an acid neutralizing agent. The major component of the subject composition is the aqueous salt solution. Although pure water does solvate the secretion deposits to a limited degree, a salt solution is more effective. Preferably, the salt containing aqueous solution is a normal saline solution.

Mixed with the subject aqueous salt solution is a polyalcohol. Usually, the polyalcohol is a short and unbranched carbon chain molecule, preferably glycerin (glycerol or 1,2,3-propanetriol). The glycerin aids in solvating a secretion deposit and is usually present from about 5% to about 15% and preferably from about 7.5% to about 9.5% by volume of the subject composition.

Further, the subject composition comprises hydrogen peroxide. When hydrogen peroxide decomposes it yields oxygen gas and water. The bubbling action of the oxygen gas that is liberated upon the decomposition aids in loosening the secretion deposits and in killing susceptible bacteria. The hydrogen peroxide may be added to the subject composition in any convenient form. Since a standard preparation of hydrogen peroxide consists of an aqueous 3% hydrogen peroxide solution, the preferred method of preparation involves the addition of this aqueous 3% solution to the other ingredients. The aqueous hydrogen peroxide solution (containing about 3% hydrogen peroxide) is usually present from about 5% to about 15% and preferably from about 7.5% to about 9.5% by volume of the subject composition.

Hydrogen peroxide tends to decompose upon standing, especially in the presence of materials that act as catalysts for the decomposition. To limit the premature loss of substantial quantities of the hydrogen peroxide in the subject composition, usually the aqueous hydrogen peroxide solution is added to the subject mixture just prior to use. Generally, addition of the hydrogen peroxide on the day the subject composition will be used is acceptable.

Also, an acid neutralizing agents is in the subject cleansing composition. Saliva is usually alkaline and this feature is maintained by the presence of the acid neutralizing agent. The acid neutralizing agent is usually present from about 5% to about 15% and preferably from about 7.5% to about 9.5% by volume of the subject composition. Preferably, the acid neutralizing agent is a liquid antacid. Such antacids include, either singly or in combination, as the active acid neutralizing component magnesium hydroxide, aluminum hydroxide, sodium bicarbonate, aluminum oxycarbonate, dihydroxyaluminum sodium carbonate, dihydroxyaluminum aminoacetate, aluminum phosphate, calcium carbonate, magnesium oxide, magaldrate, magnesium trisilicate, and equivalent substances. Commercial preparations containing such acid neutralizing components are readily available and include MAALOX®, RIOPAM®, MILANTIN®, and similar compositions. For example, MAALOX®, (MAALOX® is a federally registered trademark of the Rorer Pharmaceutical Corporation, Fort Washington, Pa 19034) contains as active acid neutralizing ingredients magnesium hydroxide and aluminum hydroxide. Additionally, MAALOX® contains as inactive components citric acid, methylparaben, natural flavor, propylparaben, saccharin sodium, sorbital, purified water, and other ingredients.

EXAMPLE 1

A portion of the subject composition was prepared by adding into 90 ml of normal saline solution, 10 ml of the antacid MAALOX® with mixing. To this was added 10 ml of glycerin and 10 ml of 3% aqueous hydrogen peroxide solution. This combination of ingredients gave the subject composition a formulation or makeup of about 8.3% MAALOX®, about 8.3% glycerin, about 8.3% aqueous 3% hydrogen peroxide solution, and about 75% normal saline solution.

EXAMPLE 2

Employing the subject composition prepared in Example 1, the subject composition was applied to wet a cleaning swab. A patient was selected that suffered from excessive deposits of dried secretions in and about the mouth. Gently, the patient's mouth and tongue were wiped with the wetted swab. The dried secretions began to dissolve and were removed by adherence to the swab. After repeating this process the dried secretion were substantially eliminated, leaving a clean mouth and tongue.

The invention has now been explained with reference to specific embodiments. Other embodiments will be suggested to those of ordinary skill in the appropriate art upon review of the present specification.

Although the foregoing invention has been described in some detail by way of illustration and examples for purposes of clarity of understanding, it will be obvious that certain changes and modifications may be practiced within the scope of the appended claims.

What is claimed is:

1. A method or removing dried secretions from the mouth and tongue of a patient suffering from dry mouth, or insufficient salvation, resulting in inordinate secretion deposits, comprising the steps of:
    a) wetting a swab with a cleansing composition comprising a normal saline solution containing glycerin, aqueous hydrogen peroxide solution having about 3% hydrogen peroxide, and a liquid antacid acid neutralizing agent;
    b) wiping said patient's mouth and tongue with said wetted swab to loosen or dissolve the dried secretions for removal by said swab; and
    c) repeating the prior steps until the dried secretions are substantially removed by adherence to said swab.

2. A method according to claim 1, wherein said glycerin constitutes about 5% to about 15% by volume of the composition.

3. A method according to claim 1, wherein said aqueous hydrogen peroxide solution constitutes about 5% to about 15% by volume of the composition.

4. A method according to claim 1, wherein said acid neutralizing agent is a liquid antacid that constitutes about 5% to about 15% by volume of the composition.

5. A method according to claim 4, wherein said liquid antacid contains an ionic compound.

6. A method according to claim 4, wherein said liquid antacid contains magnesium hydroxide and aluminum hydroxide.

7. A method according to claim 1, comprising an additional step of adding said aqueous hydrogen peroxide solution to produce said cleansing composition just prior to use for dried secretion removal to prevent premature substantial loss of oxygen from the decomposition of said hydrogen peroxide.

* * * * *